(12) United States Patent
McGuigan et al.

(10) Patent No.: US 8,263,575 B2
(45) Date of Patent: Sep. 11, 2012

(54) PHOSPHORAMIDATE DERIVATIVES OF NUCLEOSIDE COMPOUNDS FOR USE IN THE TREATMENT OF CANCER

(75) Inventors: Christopher McGuigan, Cardiff (GB); Kenneth Mills, Cardiff (GB); Costantino Congiatu, Porto Torres (IT)

(73) Assignee: Nucana Biomed Limited, Camberly, Surrey (GB)

( * ) Notice: Subject to any disclaimer, the term of this patent is extended or adjusted under 35 U.S.C. 154(b) by 740 days.

(21) Appl. No.: 11/886,931

(22) PCT Filed: Mar. 16, 2006

(86) PCT No.: PCT/GB2006/000932
§ 371 (c)(1),
(2), (4) Date: Jan. 14, 2009

(87) PCT Pub. No.: WO2006/100439
PCT Pub. Date: Sep. 28, 2006

(65) Prior Publication Data
US 2009/0215715 A1    Aug. 27, 2009

(30) Foreign Application Priority Data
Mar. 21, 2005  (GB) .................................. 0505781.5

(51) Int. Cl.
*A61K 31/70* (2006.01)
*C07H 19/20* (2006.01)

(52) U.S. Cl. ...................... 514/47; 536/26.7; 536/26.71

(58) Field of Classification Search .................. None
See application file for complete search history.

(56) References Cited

U.S. PATENT DOCUMENTS

| | | | | |
|---|---|---|---|---|
| 6,455,513 B1 * | 9/2002 | McGuigan et al. | ............. | 514/81 |
| 6,638,919 B2 * | 10/2003 | McGuigan et al. | ............. | 514/81 |
| 7,018,989 B2 * | 3/2006 | McGuigan et al. | ............. | 514/81 |
| 7,608,599 B2 * | 10/2009 | Klumpp et al. | ................. | 514/43 |
| 2003/0073618 A1 | 4/2003 | Kozhemyakin et al. | | |

FOREIGN PATENT DOCUMENTS

| | | |
|---|---|---|
| EP | 0376518 A1 | 4/1990 |
| GB | 2168353 A | 6/1986 |
| JP | 61263996 A | 11/1986 |
| JP | 02202896 A | 8/1990 |
| JP | 09249689 A | 9/1997 |
| JP | 2002104972 A | 4/2002 |
| WO | 9532984 A1 | 12/1995 |
| WO | 9633203 A1 | 10/1996 |
| WO | 2003000200 A2 | 1/2003 |
| WO | 2005012327 A2 | 2/2005 |
| WO | 2005070944 A1 | 8/2005 |

OTHER PUBLICATIONS

"Product Monograph: Leustatin". Date of Preparation: Mar. 8, 1996; Date of Revision: Jul. 31, 2006; http://www.janssen-ortho.com/JOl/pdf_files/Leustatin_E.pdf.
Griffith et al., "Enhanced Inhibition of the EDHF Phenomenon by a Phenyl Methoxyalaninyl Phosphoramidate Derivative of Dideoxyadenosine", British J Pharm 142:27-30 (2004).
Siddiqui et al., "Simple Mono-Derivatisation of the Aryl Moiety of D4A and DDA-Based Phosphoramidate Prodrugs Significantly Enhances Their Anti-HIV Potency in Cell Culture", Bioorg Med Chem Lett 9(17):2555-2560 (1999).
Reid et al., "Characterization of Transport of Nucleoside Analog Drugs by the Human Multidrug Resistance Proteins MRP4 and MRP5", Mol Pharmacol 63(5):1094-1103 (2003).
Fu et al., "Reaction of ADP with Amino Acid Methyl Esters Mediated by Trimethylsilyl Chloride", Chem Comm 1:134-135 (2003).
Fu et al., "Electrospray Ionization Mass Spectra of AMino Acid Phosphoramidates of Adenosine", Rapid Commu Mass Spectrom 14(19):1813-1822 (2000).
Ivanovskaya et al., "Modification of Oligo(Poly)Nucleotide Phosphomonoester Groups in Aqueous Solutions", Nucleosides & Nucleotides 6(5):913-934 (1987).
Ledneva et al., "Enzymic Hydrolysis of the Phosphoamide Bond of Nucleotide-(P→N)-Peptides", Doklady Akademii Nauk SSSR, 172(4):977-980 (1967) & Chemical Abstracts, Abstract No. 66:82615.
Gromova et al., "Optical Rotatory Dispersion and Circular Dichroism of Mono- and Oligonucleotide-Amino Acids (Amidates)", Biochimica et Biophysica Acta, 240(1):1-11 (1971) & Chemical Abstracts, Abstract No. 75:71336.
Tyaglov et al., Secondary Structure of Nucleotidyl-(5'.far.N)-Amino Acids Containing Different Heterocycle Bases and Amino Acids, Molekulyarnaya Biologiya (Moscow), 9(5):652-666 (1975) & Chemical Abstracts, Abstract No. 84:90528.
Juodka et al., "Oligonucleotides and Nucleotidopeptides. XXIV. Nucleotidyl (5'—N)Amino Acids as Active Amides of Nucleotides", Zhurnal Obshchei Khimii, 46(3):586-590 (1976) & Chemical Abstracts, Abstract No. 86:5721.

(Continued)

*Primary Examiner* — Lawrence E Crane
(74) *Attorney, Agent, or Firm* — Porzio, Bromberg & Newman, P.C.

(57) ABSTRACT

The compounds are phosphoramidate derivatives of nucleoside compounds such as cladribine, isocladribine, fludarabine and clofarabine useful in the treatment of cancer.

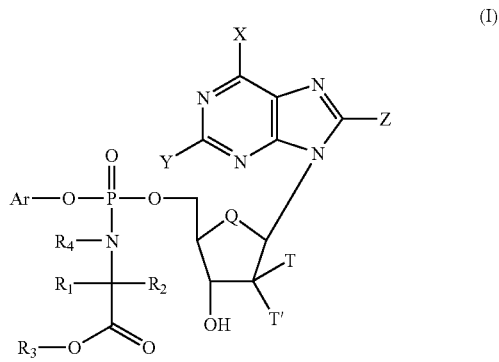

(I)

24 Claims, No Drawings

OTHER PUBLICATIONS

Zhou et al., "Simultaneous Formation of Peptides and Nucleotides from N-Phosphotheronine", Origins of Life & Evolution of the Bioshphere, 26(6):547-560 (1996) & Chemical Abstracts, Abstract No. 126:238635.

Sokolova et al., "New Method for Synthesizing Oligonucleotide Amides", Doklady Akademii Nauk SSSR, 206(1):129-131 (1972) & Chemical Abstracts, Abstract No. 78:16418.

Ryabova et al., "Synthesis of Adenylyl-5'-N-Amino Acids (or Peptides) by Means of the Carbodiimide Method", Biokhimiya (Moscow) 30(2):235-240 (1965) & Chemical Abstract, Abstract No. 63:3034b-c.

The Merck Index Thirteenth Edition 2001, pp. 29, 407-408, 729-730 and 814.

Klumpp et al., "The Novel Nucleoside Analog R14794 (4'-Azidocytidine) Is a Potent Inhibitor of NS5B-dependent RNA Synthesis and Hepatitis C Virus Replication in Cell Culture", J Biol Chem 7(281):3793-99 (2006).

Galmarini et al. "Nucleoside analogues: mechanisms of drug resistance and reversal strategies" Lukemia 15:875-890 (2001).

Weber, A.L., "Stereoselective Formation of 2'(3')-Aminoacyl Ester of a Nucleotide", J Med Evol 25(1):7-11 (1987).

Granda et al., "Isolation and Binding Properties of Leucyl-tRNA Synthetase from *Escherichia coli* MRE 600", Mol Chem Biochem 24(3):175-181 (1979).

Lohrmann, R., "Formation of Nucleoside 5'-Phosphoramidates under Potentially Prebiological conditions", J Mol Evol 10(2):137-154 (1977).

Notification of Reason for Rejection from corresponding patent application No. JP 2008-502453 mailed Jun. 1, 2012.

* cited by examiner

PHOSPHORAMIDATE DERIVATIVES OF NUCLEOSIDE COMPOUNDS FOR USE IN THE TREATMENT OF CANCER

CROSS REFERENCE TO RELATED APPLICATION

This is a National Stage of International Application No. PCT/GB2006/000932, filed Mar. 16, 2006, which claims the benefit of Application No. 0505781.5, filed in Great Britain on Mar. 21, 2005, the disclosures of which Applications are incorporated by reference herein.

The present invention relates to chemical compounds, their preparation and their use in the treatment of cancer. Particularly, although not exclusively, the present invention relates to chemical compounds useful in the treatment of leukaemia in *homo sapiens*.

Some modified purine nucleosides are known to display potent biological properties, including chemotherapeutic potential. Known clinical anti-cancer agents include cladribine and fludarabine, and also clofarabine which is in clinical development.

The following formulae show the chemical structures of cladribine, isocladribine, fludarabine and clofarabine:

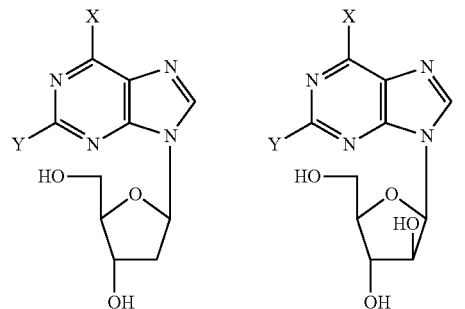

X = NH$_2$, Y = Cl cladribine
X = Cl, Y = NH$_2$ 'isocladribine'
X = NH$_2$, Y = F fludarabine

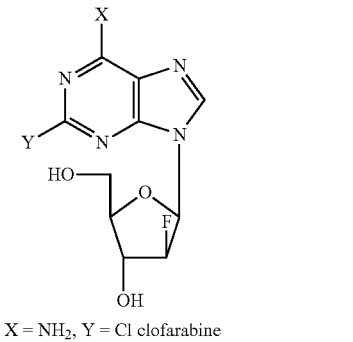

X = NH$_2$, Y = Cl clofarabine

Cladribine is a useful, but toxic drug. It is given by infusion for the treatment of leukaemias, and hairy cell leukaemia in particular (BNF, 2004). It is also used for chronic lymphocytic leukaemia in patients who have failed standard regimens with alkylating agents.

Fludarabine is licensed for the treatment of advanced B-cell chronic lymphocytic leukaemia.

Clofarabine is third line treatment in paediatric lymphoblastic leukaemia in the United States and has activity in acute myeloid leukaemia.

The structural isomer of cladribine, 'isocladribine' above, is known as a synthetic intermediate, but its biological properties have not been reported.

As with all nucleoside analogues, these agents require intracellular kinase-mediated activation to their bio-active phosphate forms. Pre-formed phosphates cannot in general be used in therapy on account of their poor membrane permeability. In fact, fludarabine is often administered as its free 5'-monophosphate, simply to boost the water solubility, but is simply acts as a nucleoside prodrug.

It is an object of the present invention to provide a compound that, in use, has enhanced therapeutic potency, particularly potency with respect to a cancer such as leukaemia.

According to a first aspect of the present invention there is provided a compound of formula I:

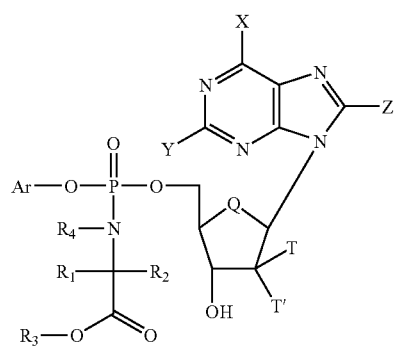

wherein:
each of X and Z is independently selected from H, OH, F, Cl, Br, I, C$_{1-6}$alkyl and NR$_5$R$_6$, where each of R$_5$ and R$_6$ is independently selected from H and C$_{1-6}$alkyl;

Y is selected from H, OH, F, Cl, Br, I, C$_{1-6}$alkyl, C$_{2-8}$alkynyl and NR$_5$R$_6$, where each of R$_5$ and R$_6$ is independently selected from H and C$_{1-6}$ alkyl;

each of T and T' is independently selected from H, F and OH, with the proviso that only one of T and T' can be OH;

Q is selected from O, S and CR$_7$R$_8$, where R$_7$ and R$_8$ are independently selected from H and C$_{1-6}$alkyl;

Ar is selected from C$_{6-30}$aryl and C$_{6-30}$heteroaryl, each of which is optionally substituted;

each of R$_1$ and R$_2$ is independently selected from H, and the group consisting of C$_{1-20}$alkyl, C$_{2-20}$alkenyl, C$_{1-20}$alkoxy, C$_{1-20}$alkoxyC$_{1-20}$alkyl, C$_{1-20}$alkoxyC$_{6-30}$aryl, C$_{2-20}$alkynyl, C$_{3-20}$cycloalkylC$_{6-30}$aryl, C$_{6-30}$aryloxy, C$_{5-20}$heterocyclyl, any of which is optionally substituted; and each of R$_3$ and R$_4$ is independently selected from H, and the group consisting of C$_{1-20}$alkyl, C$_{2-20}$alkenyl, C$_{1-20}$alkoxy, C$_{1-20}$alkoxyC$_{1-20}$alkyl, C$_{1-20}$alkoxyC$_{6-30}$aryl, C$_{2-20}$alkynyl, C$_{3-20}$cycloalkylC$_{6-30}$aryl, C$_{6-30}$aryloxy, C$_{5-20}$heterocyclyl, any of which is optionally substituted;

and pharmaceutically acceptable salts, solvates and prodrugs thereof.

Compounds embodying the present invention have surprisingly been found to have enhanced anti-cancer activity in *homo sapiens*. In particular, compounds embodying the present invention have been found to have enhanced anti-leukaemic activity compared to the known compounds cladribine, fludarabine and isocladribine. Compounds embodying the present invention are believed to have particular enhanced anti-cancer activity with respect to acute myeloid leukaemia. Compounds embodying the present invention may also be useful with respect to the prophylaxis and treatment of other types of leukaemia and other cancers, including, for example, solid tumours.

The enhanced anti-cancer activity of the compounds of the present invention is believed to be due to the membrane solubility of the phosphoramidate purine nucleosides of the present invention.

According to a further aspect of the present invention there is provided a compound of formula I for use in a method of treatment, suitably in the prophylaxis or treatment of cancer, more suitably in the prophylaxis or treatment of leukaemia.

According to a further aspect of the present invention there is provided the use of a compound of formula I in the manufacture of a medicament for the prophylaxis or treatment of cancer, preferably a medicament for the prophylaxis or treatment of leukaemia.

According to a further aspect of the present invention, there is provided a method of prophylaxis or treatment of cancer, suitably leukaemia, comprising administration to a patient in need of such treatment an effective dose of a compound of formula I.

According to a further aspect of the present invention, there is provided a pharmaceutical composition comprising a compound of formula I in combination with a pharmaceutically acceptable carrier, diluent or excipient.

According to a further aspect of the present invention there is provided a method of preparing a pharmaceutical composition comprising the step of combining a compound of formula I with a pharmaceutically acceptable excipient, carrier or diluent.

According to a further aspect of the present invention there is provided a process for the preparation of a compound of formula I, the process comprising reacting a compound of formula III:

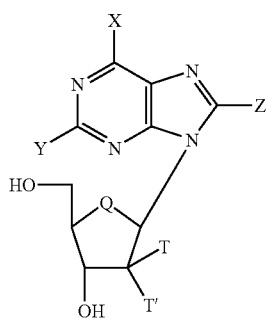

with a compound of formula IV:

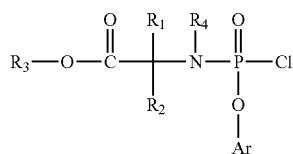

where Ar, Q, $R_1$, $R_2$, $R_3$, $R_4$, X, Y, Z, T and T' have the meanings set out above.

It is to be understood that the present invention extends to metabolic intermediates of compounds of formula I, wherein Ar is H and $R_3$ is H or $R_3$ is as defined above.

Preferably, each of X and Z is independently selected from H, OH, F, $C_1$ and $NH_2$ and Y is selected from H, OH, F, Cl, $NH_2$, and $C_{2-8}$alkynyl. Preferred compounds include those where: X is $NH_2$, Y is Cl and Z is H; X is Cl, Y is $NH_2$ and Z is H; X is $NH_2$, Y is F and Z is H; and X is $NH_2$, Y is $C_{2-8}$alkynyl, preferably $C_{2-6}$alkynyl, and Z is H.

Where Y is $C_{2-8}$alkynyl, preferably Y is linear $C_{2-6}$alkynyl and preferably Y contains one triple C≡C bond at the alpha position.

Preferably each of T and T' is H, one or preferably both of T and T' is F, or preferably T is H and T' is OH. Where one of T and T' is F, the other of T and T' is suitably H.

Preferably Q is O.

Preferably $R_4$ is H.

Preferably $R_1$ and $R_2$ are selected such that they correspond to the side chains of a natural amino acid.

Preferably one of $R_1$ and $R_2$ is Me and one of $R_1$ and $R_2$ is H, such that the C atom bearing $R_1$ and $R_2$ has chirality L as in natural alanine.

Preferably $R_3$ is alkyl, more preferably $R_3$ is selected from the group consisting of methyl, ethyl, 2-propyl, 2-butyl and benzyl, even more preferably $R_3$ is selected from the group consisting of methyl (—$CH_3$) and benzyl (—$CH_2C_6H_5$).

Preferred Ar entities include phenyl, pyridyl, naphthyl and quinolyl, each of which may be substituted or unsubstituted. Especially preferred as Ar is naphthyl, particularly unsubstituted naphthyl. Pyridyl is —$C_5H_4$. Thus by "$C_{6-30}$heteroaryl" for Ar is meant a six to thirty membered aromatic ring system that can contain one or more heteroatoms in the ring system, as further defined below.

Preferred compounds have the preferred identities for X, Y, Z, T, T', Q, Ar, $R_1$, $R_2$, $R_3$ and $R_4$ as set out above.

Particularly preferred compounds have:
X=$NH_2$, Y=Cl, Z=H, Q=O and T=T'=H and are thus derived from cladribine;
X=Cl, Y=$NH_2$, Z=H, Q=O and T=T'=H and are thus derived from isocladribine;
X=$NH_2$, Y=F, Z=H, Q=O and T=OH and T'=H and are thus derived from fludarabine;
X=$NH_2$, Y=Cl, Z=H, Q=O, T=F and T'=H and are thus derived from clofarabine; and
X=$NH_2$, Y=$C_{2-8}$alkynyl, more preferred $C_{2-6}$alkynyl, Z=H, Q=O, T=H and T'=OH.

Each of the particularly preferred compounds set out above, including those derived from cladribine, isocladribine, fludarabine and clofarabine, respectively, is especially preferred when Ar, $R_1$, $R_2$, $R_3$ and $R_4$ each has a preferred identity as set out above.

Particularly preferred compounds are set out in the Examples and in Table II below.

The phosphorus centre in compounds of formula I may be one diastereoisomer $R_p$ or $S_p$ or it may be a mixture of the diastereoisomers $R_p$ or $S_p$. Preferably it is one pure diastereoisomer. Suitably the more active diastereoisomer is selected.

Suitably the pharmaceutical acceptable salts, solvates and prodrugs of compounds of formula I are esters or amides at the 3'-OH.

Preferably the process for preparing the compound of formula I includes the step of protecting free OH groups, other than 5' on the nucleoside. The phosphorochloridate may be prepared from an aryloxy phosphorodichloridate and a suitably protected amino acid derivative. Alternatively, phosphate chemistry may be used with suitable condensing agents.

Each of Ar, $R_1$, $R_2$, $R_3$ and $R_4$ can be substituted with one, two, three, four, five or more substituents independently selected from the group comprising electron donating and electron withdrawing moieties.

Substituents on Ar can be located ortho-, meta-, para- or otherwise on the aromatic groups. Substituents on Ar are suitably independently selected from the group consisting of hydroxy, acyl, acyloxy, nitro, amino, SO₃H, SH, SR', wherein R' is independently selected from the same group set out above as $R_1$; carboxyl, $C_{1-6}$esters, $C_{1-6}$aldehyde, cyano, $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$aryl $C_{1-6}$alkyl, $C_{1-6}$alkyl$C_{5-11}$aryl, $C_{5-11}$aryl, $C_{1-6}$ fluoroalkyl and $C_{2-6}$fluoroalkenyl. Each substituent can be substituted by any other substituent.

Substituents on $R_1$, $R_2$, $R_3$ and $R_4$ are independently selected from the group consisting of hydroxy, acyl, acyloxy, nitro, amino, amido, SO₃H, SH, SR', wherein R' independently selected from the same group set out above as $R_1$, carboxy, $C_{1-6}$esters, $C_{1-6}$aldehyde, cyano, $C_{1-6}$alkylamino, $C_{1-6}$dialkylamino, thiol, chloro, bromo, fluoro, iodo, $C_{5-7}$cycloalkyl, $C_{5-7}$ cycloalkenyl, $C_{5-7}$cycloalkynyl, $C_{5-11}$aryl, $C_{5-11}$aryl$C_{1-6}$alkyl and $C_{5-20}$heterocyclyl. Each substituent can be substituted by any other substituent.

$R_1$ and $R_2$ are suitably independently selected from the group consisting of H, $C_{1-10}$alkyl, $C_{2-10}$alkenyl, $C_{2-10}$alkoxy$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{4-20}$cycloalkynyl, and $C_{5-10}$heterocyclyl.

$R_1$ and $R_2$ are suitably selected from the side chains of natural or synthetic amino acids.

$R_1$ and/or $R_2$ are preferably a side chain of a natural amino acid selected from the group consisting of glycine, alanine, valine, leucine, isoleucine, phenylalanine, tyrosine, tryptophan, serine, threonine, lysine, arginine, histidine, aspartic acid, glutamic acid, asparagines, glutamine, cysteine and methionine. Specifically, $R_1$ and/or $R_2$ are preferably selected from the group consisting of H, CH₃, —CH(CH₃)₂, —CH₂CH(CH₃)₂, —CH(CH₃)(CH₂CH₃), —CH₂Ph, —CH₂Ph-OH, —CH₂SH, —CH₂CH₂SCH₃, —CH₂OH, —CH(CH₃)(OH), —CH₂CH₂CH₂CH₂NH₃⁺, —CH₂CH₂CH₂NHC(=NH₂⁺)NH₂, —CH₂C(O)O—, —CH₂CH₂C(O)O—, —CH₂C(O)NH₂, —CH₂CH₂C(O)NH₂,

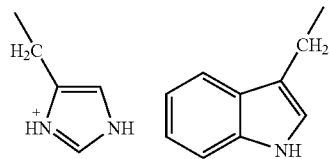

and wherein $R_1$ and $R_4$ together can form a 5-membered heterocyclic ring having the structure

$R_3$ and $R_4$ are suitably independently selected from the group consisting of H, $C_{1-10}$alkyl, $C_{2-10}$alkenyl, $C_{1-10}$alkoxy, $C_{1-10}$alkoxy$C_{1-10}$alkyl, $C_{1-10}$alkoxy$C_{6-10}$aryl, $C_{2-10}$alkynyl, $C_{3-20}$cycloalkyl, $C_{3-20}$cycloalkenyl, $C_{4-20}$cycloalkynyl, and $C_{5-20}$heterocyclyl.

$R_3$ is suitably selected from the group consisting of H, $C_{1-18}$alkyl, $C_{3-20}$cycloalkyl and benzyl.

$R_4$ is suitably selected from the group consisting of H, $C_{1-18}$alkyl, $C_{3-20}$cycloalkyl and $C_{5-20}$heterocyclyl. $R_4$ is particularly suitably selected from the group consisting of H, methyl, ethyl, propyl, butyl, pentyl, hexyl and cyclohexyl.

In a preferred embodiment, $R_1$ and $R_2$ are methyl or are linked to form a closed 5-membered heterocyclic or carbocyclic ring, for example, as present in proline.

As used herein, the term "alkyl" refers to a straight or branched saturated monovalent cyclic or acyclic hydrocarbon radical, having the number of carbon atoms as indicated (or where not indicated, an acyclic alkyl group preferably has 1-20, more preferably 1-6, more preferably 1-4 carbon atoms and a cyclic alkyl group preferably has 3-20, preferably 3-10, more preferably 3-7 carbon atoms), optionally substituted with one, two, three or more substituents independently selected from the group set out above with respect to substituents that may be present on $R_1$, $R_2$, $R_3$ and $R_4$. By way of non-limiting examples, suitable alkyl groups include methyl, ethyl, propyl, butyl, pentyl, hexyl, octyl, nonyl and decyl.

As used herein, the term "alkenyl" refers to a straight or branched unsaturated monovalent acyclic or cyclic hydrocarbon radical having one or more C=C double bonds and having the number of carbon atoms as indicated (or where not indicated, an acyclic alkenyl group preferably has 2-20, more preferably 2-6, more preferably 2-4 carbon atoms and a cyclic alkenyl group preferably has 4-20, more preferably 4-6 carbon atoms), optionally substituted with one, two, three or more substituents independently selected from the group set out above with respect to substituents that may be present on $R_1$, $R_2$, $R_3$ and $R_4$. By way of non-limiting examples, suitable alkenyl groups include vinyl, propenyl, butenyl, pentenyl and hexenyl.

As used herein, the term "alkynyl" refers to a straight or branched unsaturated monovalent acyclic or cyclic hydrocarbon radical having one or more triple C≡C bonds and having the number of carbon atoms as indicated (or where not indicated, an acyclic alkynyl group preferably has 2-20, more preferably 2-6, more preferably 2-4 carbon atoms and a cyclic alkynyl group preferably has 7-20, more preferably 8-20 carbon atoms), optionally substituted with one, two, three or more substituents independently selected from the group set out above with respect to substituents that may be present on $R_1$, $R_2$, $R_3$ and $R_4$.

As used herein, the term "alkoxy" refers to the group alkyl-O—, where alkyl is as defined above and where the alkyl moiety may optionally be substituted by one, two, three or more substituents as set out above for alkyl. By way of non-limiting examples, suitable alkoxy, groups include methoxy, ethoxy, n-propoxy, iso-propoxy, n-butoxy, tert-butoxy, sec-butoxy, n-pentoxy, n-hexoxy and 1,2-dimethylbutoxy.

As used herein, the term "aryloxy" refers to the group aryl-O—, where aryl is as defined below and where the aryl moiety may optionally be substituted by one, two, three or more substituents as set out above with respect to the group Ar.

As used herein, the term "alkoxyalkyl" refers to an alkyl group having an alkoxy substituent. Binding is through the alkyl group. The alkyl moiety and the alkoxy moiety are as defined herein with respect to the definitions of alkyl and alkoxy, respectively. The alkoxy and alkyl moieties may each be substituted by one, two, three or more substituents as set out above with regard to the definition of alkyl.

As used herein, the term "alkoxyaryl" refers to an aryl group having an alkoxy substituent. Binding is through the aryl group. The alkoxy moiety and the aryl moiety are as defined herein with respect to the definitions of alkoxy and aryl, respectively. The alkoxy and aryl moieties may each be substituted by one, two, three or more substituents, as defined herein with regard to the definitions of alkoxy and aryl, respectively.

As used herein, the term "cycloalkylaryl" refers to an aryl group having a cyclic alkyl substituent. Binding is through the aryl group. The cycloalkyl moiety and the aryl moiety are as defined herein with respect to the definitions of cycloalkyl and aryl, respectively. The cycloalkyl moiety and the aryl moiety may each be optionally substituted by one, two, three or more substituents as set out herein with regard to the definitions of alkyl and aryl, respectively.

As used herein, the term "aryl" refers to a monovalent unsaturated aromatic carbocyclic radical having one, two, three, four, five or six rings, preferably one, two or three rings, which may be fused or bicyclic. An aryl group may optionally be substituted by one, two, three or more substituents as set out above with respect to optional substituents that may be present on the group Ar. Preferred aryl groups are: an aromatic monocyclic ring containing 6 carbon atoms; an aromatic bicyclic or fused ring system containing 7, 8, 9 or 10 carbon atoms; or an aromatic tricyclic ring system containing 10, 11, 12, 13 or 14 carbon atoms. Non-limiting examples of aryl include phenyl and naphthyl. Preferred substituent groups are independently selected from hydroxy, acyl, acyloxy, nitro, amino, $SO_3H$, SH, SR', wherein R' is independently selected from the same groups as $R_1$; carboxyl, cyano, $C_{1-6}$alkylamino, $C_{1-6}$dialkylamino, thiol, chloro, bromo, fluoro and iodo.

As used herein, the term "$C_{6-30}$heteroaryl" refers to a monovalent unsaturated aromatic heterocyclic 6 to 30 membered radical having one, two, three, four, five or six rings, preferably one, two or three rings, which may be fused or bicyclic, and having contained within the ring at least one heteroatom selected from the group consisting of N, O and S. Available carbon atoms and/or heteroatoms in the heteroaryl ring system may be substituted on the ring with one or more substituents as set out above with respect to the substituents that may be present on the group Ar. Preferred heteroaryl groups are: an aromatic monocyclic ring system containing six members of which at least one member is a N, O or S atom and which optionally contains one, two or three additional N atoms; an aromatic monocyclic ring having six members of which one, two or three members are a N atom; an aromatic bicyclic or fused ring having nine members of which at least one member is a N, O or S atom and which optionally contains one, two or three additional N atoms; or an aromatic bicyclic ring having ten members of which one, two or three members are a N atom. Examples include, and are not limited to, pyridyl and quinolyl.

As used herein, the term "heterocyclyl" refers to a saturated or partially unsaturated heterocyclic ring system having one, two, three, four, five or six rings, preferably one, two or three rings, which may be fused or bicyclic, and having contained within the ring or rings at least one member selected from the group consisting of N, O and S. The prefix "$C_{5-20}$" or "$C_{5-10}$" used before heterocyclyl means, respectively, a five to twenty or a five to ten membered ring system at least one of which members is selected from the group consisting of N, O and S. Preferred heterocyclyl systems are: a monocyclic ring system having five members of which at least one member is a N, O or S atom and which optionally contains one additional O atom or one, two or three additional N atoms; a monocyclic ring having six members of which one, two or three members are a N atom; a bicyclic ring system having nine members of which at least one member is a N, O or S atom and which optionally contains one, two or three additional N atoms; or a bicyclic ring system having ten members of which one, two or three members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

Available carbon atoms and/or heteroatoms of the "heterocyclyl" ring systems described above may be substituted on the ring with one or more heteroatoms. Where the ring(s) is substituted with one or more heteroatoms, heteroatom substituents are selected from oxygen, nitrogen, sulphur and halogen (F, Cl, Br and I). Where the ring(s) is substituted with one or more heteroatoms, preferably there are 1, 2, 3 or 4 heteroatom substituents selected from the group consisting of oxygen, nitrogen and/or halogen. Preferred substituent groups are independently selected from hydroxy, acyl, acyloxy, nitro, amino, $SO_3H$, SH, SR', wherein R' is independently selected from the same groups as $R_1$; carboxyl, cyano, $C_{1-6}$alkylamino, $C_{1-6}$dialkylamino, thiol, chloro, bromo, fluoro and iodo.

The process is preferably carried out in the presence of a suitable solvent.

Suitable solvents include hydrocarbon solvents such as benzene and toluene; ether type solvents such as diethyl ether, tetrahydrofuran, diphenyl ether, anisole and dimethoxybenzene; halogenated hydrocarbon solvents such as methylene chloride, chloroform and chlorobenzene; ketone type solvents such as acetone, methyl ethyl ketone and methyl isobutyl ketone; alcohol type solvents such as methanol, ethanol, propanol, isopropanol, n-butyl alcohol and tert-butyl alcohol; nitrile type solvents such as acetonitrile, propionitrile and benzonitrile; ester type solvents such as ethyl acetate and butyl acetate; carbonate type solvents such as ethylene carbonate and propylene carbonate; and the like. These may be used singly or two or more of them may be used in admixture.

Preferably an inert solvent is used in the process of the present invention. The term "inert solvent" means a solvent inert under the conditions of the reaction being described in conjunction therewith including, for example, benzene, toluene, acetonitrile, tetrahydrofuran, dimethylformamide, chloroform, methylene chloride (or dichloromethane), diethyl ether, ethyl acetate, acetone, methylethyl ketone, methanol, ethanol, propanol, isopropanol, tert-butanol, dioxane, pyridine, and the like. Tetrahydrofuran is particularly preferred.

Preferably the process of the present invention is carried out under substantially dry conditions.

As used herein, the term "stereoisomer" defines all possible compounds made up of the same atoms bonded by the same sequence of bonds but having different three-dimensional structures which are not interchangeable, which the compounds of the present invention may possess.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in stereochemically mixed form or individual enantiomers may be prepared by standard techniques known to those skilled in the art, for example, by enantiospecific synthesis or resolution, formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

Furthermore, it should be appreciated that the phosphate centre is chiral in the compounds of the present invention and the compounds may exist as Rp and Sp diastereoisomers. The composition of the compound may be mixed Rp and Sp or one pure diastereomer. Preferably the compound is a substantially pure single isomer.

There may be a mixture of 1:1 Rp to Sp diastereomers. Alternatively, there may be a ratios of 1:2, 1:3, 1:4, 1:5, 1:6, 1:7, 1:8, 1:9, 1:10, 1:15, 1:20, 1:50 or 1:100 of Rp to Sp diastereomers or vice versa.

The term "solvate" means a compound of as defined herein, or a pharmaceutically acceptable salt of a compound of structure (I) or (II), wherein molecules of a suitable solvent are incorporated in the crystal lattice. A suitable solvent is physiologically tolerable at the dosage administered.

Examples of suitable solvents are ethanol, water and the like. When water is the solvent, the molecule is referred to as a hydrate.

The compounds of the present invention may also be present in the form of pharmaceutical acceptable salts. For use in medicine, the salts of the compounds of this invention refer to non-toxic "pharmaceutically acceptable salts." FDA approved pharmaceutical acceptable salt forms (Ref. International J. Pharm. 1986, 33, 201-217; J. Pharm. Sci., 1977, January, 66 (1)) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, maleate, mandelate, mesylate, methylbromide, methylnitrate, methylsulfate, mucate, napsylate, nitrate, pamoate, pantothenate, phosphate, phosphate, polygalacturonate, salicylate, stearate, subacetate, succinate, sulfate, tannate, tartrate, teoclate, tosylate and triethiodide.

Pharmaceutically acceptable basic/cationic salts include, and are not limited to aluminum, benzathine, calcium, chloroprocaine, choline, diethanolamine, ethylenediamine, lithium, magnesium, potassium, procaine, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Pharmaceutically acceptable ester derivatives in which one or more free hydroxy groups are esterified in the form of a pharmaceutically acceptable ester are particularly prodrug esters that may be convertible by solvolysis under physiological conditions to the compounds of the present invention having free hydroxy groups.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

The compound having formula I or pharmaceutical composition according to the present invention can be administered to a patient, which may be *homo sapiens* or animal, by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogram body weight of recipient per day, a more preferred lower dose is 1 mg per kilogram body weight of recipient per day. A suitable dose is preferably in the range of 1 to 50 mg per kilogram body weight per day, and more preferably in the range of 1 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

EXAMPLES

Target compounds were prepared by reacting the appropriate nucleoside with the required phosphorochloridate. The latter reagents were prepared by published methods from aryl phosphorodichloridates with amino acid ester hydrochlorides. Several examples are given.

Synthesis of 2-chloro-2'-deoxyadenosine-5'-[phenyl-(methoxy-L-alaninyl)]-phosphate (CPF203)

N-Methylimidazole (NMI) (0.29 g, 3.50 mmol, 0.29 mL) was added to a stirring suspension of 2-chloro-2'-deoxyadenosine (0.200 g, 0.70 mmol) in dry THF (10 mL). Phenyl-(methoxy-L-alaninyl)-phosphorochloridate (0.58 g, 2.10 mmol) in dry THF was added dropwise at −78° C. After 15 min the reaction was let to rise to room temperature. The reaction was followed by TLC (DCM/MeOH 95/5), after 4 hours further Phenyl-(methoxy-L-alaninyl) phosphorochloridate (0.28 g, 1.0 mmol) was added and the reaction was left stirring overnight. MeOH was added to quench the reaction, volatiles were evaporated and the residue was purified by flash chromatography (DCM/MeOH 100/0 to 95/5) and preparative TLC (DCM/MeOH 96/4) to give the product as white foam (0.008 g, 2% yield; Cladribine recovered 0.15 g). $^{31}$P-NMR (CDCl$_3$, 121 MHz): δ 4.56, 4.21. $^1$H-NMR (CDCl$_3$, 300 MHz): δ 8.14, 8.07 (1H, 2s, H-8), 7.52-7.29 (5H, m, Ph), 6.56-6.50 (1H, m, H-1'), 6.18-6.01 (1H, bs, NH$_2$), 4.90-4.77 (1H, m, H-3'), 4.46-4.56 (2H, m, H-5'), 4.32-4.26 (1H, m, H-4'), 4.22-4.02 (1H, m, CHNH), 3.85, 3.83 (3H, 2 s, CH$_3$O), 2.92-2.61 (2H, m, H-2'), 1.56-1.44 (3H, m, CH$_3$CH).

Synthesis of 2-chloro-2'-deoxyadenosine-5'-[phenyl-(benzoxy-L-alaninyl)]-phosphate (CPF204)

NMI (0.29 g, 3.50 mmol, 0.29 mL) was added to a stirring suspension of 2-chloro-2'-deoxyadenosine (0.200 g, 0.70 mmol) in dry THF (10 mL). Phenyl-(benzoxy-L-alaninyl)-phosphorochloridate (0.74 g, 2.10 mmol) in dry THF was added dropwise at −78° C. After 15 min the reaction was let to rise to room temperature and the reaction was left stirring overnight. MeOH was added to quench the reaction, volatiles were evaporated. The residue was purified by flash chromatography (DCM/MeOH 100/0 to 95/5) and preparative TLC (DCM/MeOH 96/4) to give the product as white foam (0.015 g, 4% yield). $^{31}$P-NMR (MeOH, 121 MHz): δ 5.11, 4.81. $^1$H-NMR (MeOH, 300 MHz): δ 8.12, 8.10 (1H, 2 s, H-8), 7.23-7.04 (10H, m, PhO, PhCH$_2$), 6.30-6.24 (1H, m, H-1'), 5.04-5.00 (2H, m, PhCH$_2$), 4.52-4.48 (1H, m, H-3'), 4.29-4.15 (2H, m, H-5'), 4.08-4.04 (1H, m, H-4'), 3.91-3.81 (1H, m, CHNH), 2.63-2.54 (1H, m, one of H-2'), 2.41-2.33 (1H, m, one of H-2'), 1.24-1.17 (3H, m, CHCH$_3$). $^{13}$C-NMR (MeOD; 75 MHz): δ 20.6, 20.8 (CH$_3$), 41.2 (C-2'), 52.0, 52.1 (CHCH$_3$), 67.7, 68.1, 68.2, 68.3 (C-5', CH$_2$Ph), 72.6 (C-3'), 86.2, 86.4 (C-1'), 87.2, 87.3 (C-4'), 121.7, 121.8, 126.5, 129.6, 129.7, 129.9, 131.1, 137.6, 141.5 (C-5, C-8, PhCH$_2$, PhO, "ipso" PhCH$_2$), 151.8, 151.9 (C-6), 152.4, 152.5 ("ipso" PhO), 155.7, 155.8 (C-2), 158.4 (C-4), 175.0, 175.2 (COOCH$_2$Ph).

Synthesis of 2-chloro-2'-deoxyadenosine-5'-[1-naphthyl-(benzoxy-L-alaninyl)]-phosphate NMI (0.29 g, 3.50 mmol, 0.29 mL) was added to a stirring suspension of 2-chloro-2'-deoxyadenosine (0.200 g, 0.70 mmol) in dry THF (6 mL). 1-Naphthyl-(benzoxy-L-alaninyl)-phosphorochloridate (0.85 g, 2.10 mmol) in dry THF (4 mL) was added dropwise at −78° C. After 15 min the reaction was allowed to rise to room temperature and left stirring overnight. MeOH was added to quench the reaction, volatiles were evaporated. The residue was purified by flash chromatography (DCM/MeOH 100/0 to 95/5) and by preparative HPLC (H$_2$O/CH$_3$CN 60/40) to give the product as white foam (mixed. 26 mg, fast eluting. 11 mg, slow eluting. 8 mg).
Mixed (CPF210)
$^{31}$P-NMR (CDCl$_3$, 202 MHz): δ 3.64, 3.23 (int.: 1.00, 0.97).
HPLC: Rt 8.92, 9.59 min. $^1$H-NMR (CDCl$_3$, 500 MHz): δ 8.00-7.98 (1H, m, H-8 Naph), 7.86 (0.5H, s, one of H-8 of one diastereoisomer), 7.77 (1H, d, H-5 Naph, $^3$J=7.4 Hz), 7.75 (0.5H, s, one of H-8 of one diastereoisomer), 7.56 (1H, d, H-4 Naph, $^3$J=8.3 Hz), 7.44-7.40 (3H, m, H-2 Naph, H-6 Naph, H-7 Naph), 7.31-7.15 (6H, m, H-3 Naph, Ph), 6.25-6.21 (1H, m, H-1'), 5.73 (2H, bs, NH$_2$), 5.04 (1H, s, CH$_2$Ph of one diastereoisomer), 4.97 (0.5H, d, $^2$J=12.2 Hz, one CH$_2$Ph of one diastereoisomer), 4.94 (0.5H, d, $^2$J=12.2 Hz, one CH$_2$Ph of one diastereoisomer), 4.57-4.54 (0.5H, m, H-3' of one diastereoisomer), 4.49-4.46 (0.5H, m, H-3' of one diastereoisomer), 4.34-4.23 (2H, m, H-5'), 4.11-4.00 (2H, m, H-4', CHNH), 3.91 (0.5H, CHNH of one diastereoisomer), 3.90 (0.5H, CHNH of one diastereoisomer), 3.13 (0.5H, OH of one diastereoisomer), 3.01 (0.5H, OH of one diastereoisomer), 2.56-2.51 (0.5H, m, one H-2' of one diastereoisomer), 2.43-2.29 (1.5H, m, three H-2'), 1.27-1.24 (3H, d, CHCH$_3$).
$^{13}$C-NMR (CDCl$_3$; 125 MHz): δ 19.7, 19.8 (CH$_3$), 38.8 (C-2'), 49.4, 49.5 (CHCH$_3$), 64.8, 66.2, 66.3 (C-5', CH$_2$Ph), 69.8 (C-3'), 83.0 (C-1'), 83.9, 84.0 (C-4'), 113.9, 114.0 (C-2 Naph), 117.6, 120.2, 120.3, 123.9, 124.5, 125.2, 125.4, 125.5, 125.7, 126.8, 127.1, 127.4, 127.5, 127.6 (C-5, C-8, PhCH$_2$, C-5a Naph, C-3 Naph, C-4 Naph, C-5 Naph, C-6 Naph, C-7 Naph, C-8 Naph, C-8a Naph), 133.6, 133.7, 134.1 ("ipso" PhCH$_2$, C-4a Naph), 145.3 (C-1 Naph), 149.3 (C-6), 153.0 (C-2), 155.13 (C-4), 172.4 (COOCH$_2$Ph).
Fast Eluting (cpf211)
$^{31}$P-NMR (CDCl$_3$, 202 MHz): δ 3.60, 3.22 (int.: 4.87, 1.00). HPLC: Rt 7.59, 8.92 min. $^1$H-NMR (CDCl$_3$, 500 MHz): δ 8.03 (1H, d, $^3$J=7.5 Hz, H-8 Naph), 7.92 (0.2H, s, one of H-8 of minor diastereoisomer), 7.80 (0.8H, s, H-8), 7.79 (1H, d, $^3$J=7.4 Hz, H-5 Naph), 7.61 (1H, d, H-4 Naph, $^3$J=8.3 Hz), 7.47-7.44 (3H, m, H-2 Naph, H-6 Naph, H-7 Naph), 7.35-7.12 (6H, m, H-3 Naph, Ph), 6.29-6.26 (1H, m, H-1'), 5.88 (2H, bs, NH$_2$), 5.08 (0.4H, s, CH$_2$Ph of minor diastereoisomer), 5.05, 4.97 (1.6H, 2 d, $^2$J=12.2 Hz, CH$_2$Ph), 4.61-4.58 (0.2H, m, H-3' of minor diastereoisomer), 4.54-4.51 (0.8H, m, H-3'), 4.36-4.32 (2H, m, H-5'), 4.12-4.06 (2.2H, m, H-4', CHNH, CHNH of minor diastereoisomer), 3.82 (0.8H, CHNH), 3.32 (0.2H, OH of minor diastereoisomer), 3.25 (0.8H, OH), 2.58-2.53 (0.2H, m, one H-2' of minor diastereoisomer), 2.46-2.42 (0.2H, m, one H-2' of minor diastereoisomer), 2.41-2.33 (1.6H, m, H-2'), 1.31-1.29 (3H, 2 d, CHCH$_3$).
Slow Eluting (cpf212) $^{31}$P-NMR (CDCl$_3$, 202 MHz): δ 3.64, 3.25 (int.: 1.00, 28.15). HPLC: Rt 9.59, 10.92 min. $^1$H-NMR (CDCl$_3$, 500 MHz): δ 7.99-7.97 (1H, dd, H-8 Naph), 7.87 (1H, s, H-8), 7.77-7.74 (1H, m, H-5 Naph), 7.57 (1H, d, H-4 Naph, $^3$J=8.3 Hz), 7.44-7.40 (3H, m, H-2 Naph, H-6 Naph, H-7 Naph), 7.29-7.20 (6H, m, H-3 Naph, Ph), 6.23 (1H, m, H-1'), 5.81 (2H, bs, NH$_2$), 5.03 (2H, s, CH$_2$Ph), 5.00, 4.92 (d, $^2$J=12.3 Hz, CH$_2$Ph of minor diastereoisomer), 4.58-4.55 (1H, m, H-3'), 4.49, 4.48 (m, H-3' of minor diastereoisomer), 4.34-4.23 (2H, m, H-5'), 4.08-3.99 (3H, m, H-4', CHNH, CHNH$_2$), 3.78 (CHNH of minor diastereoisomer), 3.31 (1H, bs, OH), 2.56-2.50 (1H, m, one H-2'), 2.42-2.38 (1H, m, one H-2'), 2.37-2.31 (m, H-2' of minor diastereoisomer), 1.26 (3H, 2 d, CHCH$_3$).

Synthesis of 2-chloro-2'-deoxyadenosine-5'-[4-chloro-1-naphthyl-(benzoxy-L-alaninyl)]-phosphate (CPF218)

NMI (0.26 g, 3.20 mmol, 0.25 mL) was added to a stiffing suspension of 2-chloro-2'-deoxyadenosine (0.183 g, 0.64 mmol) in dry THF (6 mL).
4-Chloro-1-naphthyl-(benzoxy-L-alaninyl)-phosphochloridate (0.87 g, 1.92 mmol) in dry THF (4 mL) was added dropwise at −78° C. After 15 min the reaction was allowed to rise to room temperature and left stirring overnight.
MeOH was added to quench the reaction, volatiles were evaporated. The residue was purified by flash chromatography (DCM/MeOH 100/0 to 95/5) and by preparative HPLC (H$_2$O/CH$_3$CN 60/40) to give the product as white foam (15 mg, 3%). $^{31}$P-NMR (CDCl$_3$, 202 MHz): δ 3.45, 3.26. HPLC: Rt 7.92, 10.20 min.
$^1$H-NMR (CDCl$_3$, 500 MHz): δ 8.14-8.10 (1H, m, H-5 Naph), 7.99-7.96 (1H, m, H-8 Naph), 7.88 (0.5H, s, one of H-8 of one diastereoisomer), 7.82 (0.5H, s, one of H-8 of one diastereoisomer), 7.54-7.49 (1H, m, H-6 Naph), 7.47-7.40 (1H, m, H-7 Naph), 7.32-7.14 (7H, m, H-2 Naph, H-3 Naph, Ph), 6.25-6.22 (1H, m, H-1'), 6.04 (2H, bs, NH$_2$), 5.00 (1H, s, CH$_2$Ph of one diastereoisomer), 4.97 (0.5H, d, $^2$J=12.2 Hz, one CH$_2$Ph of one diastereoisomer), 4.90 (0.5H, d, $^2$J=12.2 Hz, one CH$_2$Ph of one diastereoisomer), 4.59-4.54 (1H, m, H-3'), 4.33-4.19 (2.5H, m, H-5', CHNH of one diastereoisomer), 4.08-3.96 (2.5H, m, H-4', CHNH, CHNH of one diastereoisomer), 3.61, 3.57 (1H, 2 bs, OH-3'), 3.01 (0.5H, OH of one diastereoisomer), 2.59-2.34 (2H, m, H-2'), 1.25-1.23 (3H, m, CHCH$_3$). $^{13}$C-NMR (CDCl$_3$; 125 MHz): δ 20.8 (CH$_3$), 39.7 (C-2'), 50.5 (CHCH$_3$), 66.2, 66.3 (C-5'), 67.4 (CH$_2$Ph), 71.0 (C-3'), 84.1 (C-1'), 84.9, 85.0, 85.1 (C-4'), 114.8, 114.9, 115.1, 118.8, 121.8, 124.7, 125.5, 127.2, 127.8, 128.1, 128.3, 128.5, 128.6, 128.7 (C-2 Naph, C-3 Naph, C-4 Naph, C-5 Naph, C-6 Naph, C-7 Naph, C-8 Naph, C-8a Naph, Ph), 131.6 (C-4a), 135.0 ("ipso" PhCH$_2$), 139.3, 139.4 (C-8), 145.3, 145.4 (C-1 Naph), 150.4 (C-6), 154.1 (C-2), 156.1 (C-4), 173.3 (COOCH$_2$Ph).

Synthesis of 2-amino-6-chloropurine-2'-deoxyriboside-5'-[phenyl-(benzoxy-L-alaninyl)]-phosphate NMI (0.36 g, 4.40 mmol, 0.35 mL) was added to a stirring suspension of 6-chloro-2'-deoxyguanosine (0.25 g, 0.88 mmol) and Phenyl-(benzoxy-L-alaninyl)-phosphorochloridate (0.93 g, 2.64 mmol) in dry THF (10 mL) at −78° C. After 15 min the reaction was let to rise to room temperature and the reaction was left stirring overnight. MeOH was added to quench the reaction, volatiles were evaporated. The residue was purified by flash chromatography (DCM/MeOH 100/0 to 96/4) and preparative TLC (DCM/MeOH 97/3) to give the product as white foam (0.145 g, 27.0% yield). $^{31}$P-NMR (MeOH, 121 MHz): δ 5.33, 5.00. $^1$H-NMR (MeOH, 300 MHz): δ 8.17, 8.16 (1H, 2 s, H-8), 7.32-7.13 (10H, m, PhO, PhCH$_2$), 6.37, 6.32 (1H, 2 d, H-1'), 5.11-5.06 (2H, m, PhCH$_2$), 4.61-4.56 (1H, m, H-3'), 4.41-4.20 (1H, m, H-5'), 4.18-4.08 (1H, m, H-4'), 4.00-3.89 (1H, m, CHNH), 2.84-2.68 (1H, m, one of H-2'), 2.41-2.30 (1H, m, one of H-2'), 1.30-1.24 (3H, m, CHCH$_3$). $^{13}$C-NMR (MeOD; 75 MHz): δ 20.6, 20.7, 20.8 (CH$_3$), 40.4, 40.7 (C-2'), 51.9, 52.1 (CHCH$_3$), 67.8, 68.1, 68.4 (C-5', CH$_2$Ph), 72.8 (C-3'), 86.4 (C-1'), 87.1, 87.3, 87.4 (C-4'), 121.7, 121.8, 125.8, 126.5, 129.7, 129.9, 131.1 (PhCH$_2$, PhO), 137.5, 137.6 ("ipso" PhCH$_2$), 143.2, 143.3 (C-8), 152.0 (C-6), 152.4, 152.5 ("ipso" PhO), 155.0, 155.1 (C-2), 161.9 (C-4), 175.0, 175.2 (COOCH$_2$Ph).

Synthesis of 9-β-D-arabinofuranosyl-2-fluoroadenine-5'-[phenyl-(methoxy-L-alaninyl)]phosphate (CPF109)

9-β-D-arabinofuranosyl-2-fluoroadenine (50.0 mg, 0.175 mmol) was co-evaporated twice with toluene, dissolved in 6 mL of THF/Pyridine (mixture 2:1 respectively) and NMI (71.8 mg, 0.875 mmol, 70 µL) was added. The mixture was cooled at −17° C. in ice/salt bath and under inert atmosphere a solution 1M in THF of phenyl-(methoxy-L-alaninyl) phosphorochloridate (145.8 mg, 0.525 mmol, 525 µL) was added dropwise over 1 hr. After 1 hr the reaction was left to raise to room temperature, stirred for 16 hr then quenched with methanol. The solvent was removed under reduce pressure and the crude purified by flash column chromatography using dichloromethane/methanol (gradient elution from 95:5 to 85:5). The isolated compound was further purified by preparative thin layer chromatography using as solvent Chloroform/methanol (94:6) to give the product as a clear, colourless oil, which solidified to a white foam after trituration and co-evaporation with diethyl ether (9.5 mg, 10.3%).

$^{19}$F-NMR (MeOD; 282 MHz): δ −54.04. $^{31}$P-NMR (MeOD; 121 MHz): δ 4.99. $^1$H-NMR (MeOD; 300 MHz): δ 8.22, 8.20 (1H, 2×s, H-8), 7.38-7.19 (5H, m, PhO), 6.33, 6.32 (1H, 2×d, $^3$J=3.4 Hz, H-1') 4.89-4.27 (4H, m, H-2'+H-5'+H-4'), 4.17-4.03 (1H, m, H-3'), 4.00-3.85 (1H, m, CHCH$_3$), 3.66-3.65 (3H, 2×s, CH$_3$O), 1.34, 1.29 (3H, 2×d, $^3$J=7.1 Hz, CH$_3$CH). $^{13}$C-NMR (MeOD; 75 MHz): δ 20.7, 20.8, 20.9 (CH$_3$CH), 51.9 (CH$_3$CH), 53.1, 53.2 (CH$_3$O), 67.4, 67.5, 67.8, 67.9 (C-5'), 77.3, 77.4, 77.6 (C-4'+C-2'), 84.0, 84.1, 84.2, 84.3 (C-3'), 86.5, 86.7 (C-1'), 118.2 (adenosine-C), 121.8, 121.9 ('m', PhO), 126.5 ('p', PhO), 131.1 ('ipso', PhO), 142.9, 143.0 ($^5$J=2.9 Hz, C-8), 142.8, 142.9 (C-8), 152.4, 152.5, 152.6 (adenosine-C+'ipso' PhO), 159.2, 159.4, 159.6, 162.4 (adenosine-C), 175.7, 175.8, 175.9 (COOMe).

Synthesis of 2-chloro-2'-beta-fluoro-(2'-deoxyadenosine-5'-[phenyl-(benzoxy-L-[alaninyl-]-phosphate (CPT2001)

Clofarabine-5'-[phenyl-(benzoxy-L-alaninyl)]phosphate

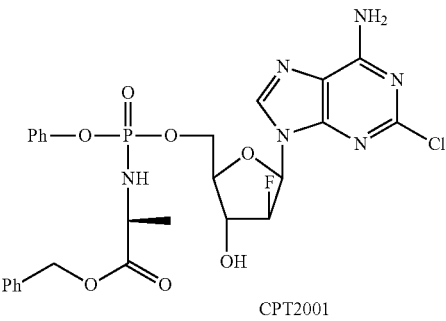

CPT2001

CPT2001 was prepared from a stirring solution of Clofarabine (0.23 g, 0.75 mmol) and phenyl-(benzoxy-L-alaninyl)-phosphorochloridate (0.80 g, 2.25 mmol) in 12.5 mL of anhydrous THF/Pyr (4/1) at −80° C. NMI (0.31 g, 300 µL, 3.75 mmol) was added dropwise over 1 min. After 15 min the reaction was left to rise to room temperature and stirred for 12 h. The solvent was removed under reduced pressure. The resulting residue was purified by flash chromatography, eluting with dichloromethane/methanol 98/2 to give the pure product as a white foamy solid (0.31, 66.0% yield).

$^{31}$P-NMR (MeOD, 202 MHz): δ 3.77, 3.64; $^{19}$F-NMR (MeOD, 470 MHz): δ −198.98, −199.01; $^1$H-NMR (MeOD, 500 MHz): δ 8.17, 8.16 (1H, 2 s, H-8), 7.34-7.15 (10H, m, PhO, PhCH$_2$), 6.46-6.40 (1H, m, H-1'), 5.21-5.07 (3H, m, H-2', PhCH$_2$), 4.56, 4.52 (1H, 2 s, H-3'), 4.40-4.39 (2H, m, H-5'), 4.19-4.16 (1H, m, H-4'), 4.04-4.01 (1H, m, CHCH$_3$), 1.35, 1.33 (3H, 2 d, $^3$J=8.5 Hz, CHCH$_3$); $^{13}$C-NMR (MeOD, 75 MHz): δ 20.3, 20.4, 20.5 (CH$_3$), 51.6, 51.8 (CHCH$_3$), 66.8, 67.1 (C-5'), 68.0 (CH$_2$Ph), 75.0, 75.1, 75.3 (C-3'), 83.6, 83.7, 83.8 (C-4'), 84.3, 84.4, 84.5 (C-1'), 95.6, 97.2 (C-2'), 118.6 (C-5), 121.4, 121.5, 126.2, 129.2, 129.3, 129.6, 130.8 (PhO, CH$_2$Ph), 137.2 ('ipso'CH$_2$Ph), 141.7, 141.8 (C-8), 151.7, 152.2 ('ipso' PhO, C-6), 155.6 (C-4), 158.1 (C-2), 174.8, 174.9 (CO$_2$CH$_2$Ph). HPLC (H$_2$O/CH$_3$CN from 100/0 to 0/100 in 20 min): t$_R$ 11.76 min. ESI MS (positive): 621 [M].

Biological Data

Compounds CPF203, CPF204, CPF194, CPF210, CPF211, CPF212, CPF218 and CPT2001 were each tested in leukaemic cell lines to assess their anti-cancer efficacy. The compounds were tested using the MTS assay reagents from Promega (CellTiter96 Aqueous One solution proliferation assay). The compounds were tested between 10 µM and 0.002 µM in four fold dilutions.

The cell lines employed are set out in Tables IA and IB below and are NB4, HL60, NB4R2, K562, KG1, and U937 leukemia cell lines.

Table IA gives the IC$_{50}$±standard deviation value for each cell line and compound tested and for all the cell lines together, in µM. Included in Table IA below, as a comparative example, is corresponding cell line data for cladribine. Table IB gives the IC$_{50}$ value for each cell line and compound tested. Included in Table IB below, as a comparative example, is corresponding cell line data for clofarabine.

TABLE IA

|        | Cladribine   | CPF203       | CPF204       | CPF194       | CPF210       | CPF211       | CPF212       | CPF218       |
|--------|--------------|--------------|--------------|--------------|--------------|--------------|--------------|--------------|
| NB4    | 9.39 ± 4.25  | 1.16 ± 0.04  | 0.23 ± 0.10  | —            | 0.24 ± 0.11  | 0.43 ± 0.04  | 0.23 ± 0.04  | 0.27 ± 0.03  |
| HL60   | 10.28 ± 3.46 | 6.23 ± 1.75  | 1.75 ± 0.89  | —            | 0.65 ± 0.19  | 1.66 ± 0.24  | 1.78 ± 0.50  | 1.75 ± 0.76  |
| NB4R2  | 7.81 ± 1.64  | 2.28 ± 0.59  | 0.63 ± 0.04  | —            | 1.03 ± 0.15  | 1.18 ± 0.21  | 1.01 ± 0.39  | 1.09 ± 0.04  |
| K562   | —            | —            | —            | —            | 2.36 ± 1.57  | 2.28 ± 1.32  | 5.80 ± 3.60  | 4.41 ± 0.95  |
| KG1    | 5.48 ± 1.86  | 2.23 ± 0.69  | 0.67 ± 0.20  | 2.64 ± 0.18  | 1.80 ± 0.72  | 2.63 ± 1.19  | 1.54 ± 0.44  | 1.56 ± 0.25  |
| U937   | 2.08 ± 2.75  | 1.29 ± 0.91  | 0.08 ± 0.01  | —            | 0.19 ± 0.09  | 0.28 ± 0.03  | 0.14 ± 0.15  | 0.55 ± 0.44  |
| All lines | 7.21 ± 3.69 | 2.64 ± 2.09 | 0.67 ± 0.70 | 2.64 ± 0.18  | 1.04 ± 1.02  | 1.41 ± 1.09  | 1.75 ± 2.34  | 1.60 ± 1.47  |

TABLE IB

|       | Clofarabine | CPT2001 |
|-------|-------------|---------|
| NB4   | 0.20        | 0.12    |
| U937  | 0.26        | 0.08    |

Table II below sets out the structures of the presently exemplified compounds embodying the present invention in terms of formula I above, with in each case Z=H and Q=O.

TABLE II

|         | X    | Y    | T' | T  | Ar         | R¹   | R² | R³         | R⁴ |
|---------|------|------|----|----|------------|------|----|------------|----|
| CPF203  | NH₂  | Cl   | H  | H  | C₆H₅       | CH₃  | H  | CH₃        | H  |
| CPF204  | NH₂  | Cl   | H  | H  | C₆H₅       | CH₃  | H  | C₆H₅CH₂    | H  |
| CPF210  | NH₂  | Cl   | H  | H  | C₁₀H₇      | CH₃  | H  | C₆H₅CH₂    | H  |
| CPF211  | NH₂  | Cl   | H  | H  | C₁₀H₇      | CH₃  | H  | C₆H₅CH₂    | H  |
| CPF212  | NH₂  | Cl   | H  | H  | C₁₀H₇      | CH₃  | H  | C₆H₅CH₂    | H  |
| CPF218  | NH₂  | Cl   | H  | H  | 4-ClC₁₀H₆  | CH₃  | H  | C₆H₅CH₂    | H  |
| CPF194  | Cl   | NH₂  | H  | H  | C₆H₅       | CH₃  | H  | C₆H₅CH₂    | H  |
| CPF109  | NH₂  | F    | H  | OH | C₆H₅       | CH₃  | H  | CH₃        | H  |
| CPT2001 | NH₂  | Cl   | H  | F  | C₆H₅       | CH₃  | H  | C₆H₅CH₂    | H  |

With regard to the data contained in Table IA, each of the compounds embodying the present invention is seen to demonstrate enhanced anti-cancer activity compared to cladribine.

Notably, compound CPF210, wherein Ar is unsubstituted naphthyl, shows greater anti-leukaemic potency than the corresponding compound CPF203, wherein Ar is unsubstituted phenyl.

Noteworthy also is the anti-leukaemic activity demonstrated by compound CPF194, which is the phosphoramidate of the known inactive compound isocladribine.

With regard to the data contained in Table IB, the compound CPT2001 embodying the present invention is seen to demonstrate enhanced anti-cancer activity compared to clofarabine.

The invention claimed is:

1. A compound of formula I:

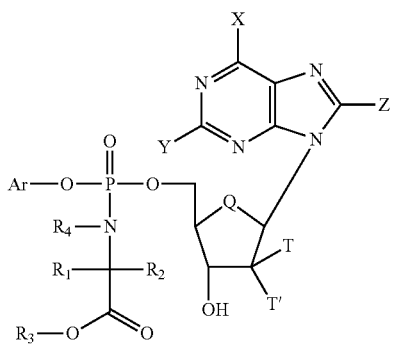

I wherein:
each of X and Z is independently selected from H, OH, F, Cl, Br, I, $C_{1-6}$alkyl and $NR_5R_6$, where each of $R_5$ and $R_6$ is independently selected from H and $C_{1-6}$alkyl;

Y is selected from OH, F, Cl, Br, I, $C_{1-6}$alkyl, $C_{2-8}$alkynyl, and $NR_5R_6$, where each of $R_5$ and $R_6$ is independently selected from H and $C_{1-6}$ alkyl;

each of T and T' is independently selected from H, F and OH, with the proviso that only one of T and T' can be OH;

Q is selected from O, S and $CR_7R_8$, where $R_7$ and $R_8$ are independently selected from H and $C_{1-6}$alkyl, Ar is selected from $C_{6-30}$aryl and $C_{6-30}$heteroaryl, each of which is optionally substituted with one or more substituents independently selected from the group consisting of hydroxy, acyl, acyloxy, nitro, amino, $SO_3H$, SH, SR', wherein R' is independently selected from the same group as $R_1$; carboxyl, $C_{1-6}$esters, $C_{1-6}$aldehyde, cyano, $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$aryl$C_{1-6}$alkyl, $C_{1-6}$alkyl$C_{5-11}$aryl, $C_{5-11}$aryl, $C_{1-6}$ fluoroalkyl and $C_{2-6}$fluoroalkenyl;

each of $R_1$ and $R_2$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;

each of $R_3$ and $R_4$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;

the optional substituents on $R_1$, $R_2$, $R_3$, and $R_4$ being one or more substituents independently selected from the group consisting of hydroxy, acyl, acyloxy, nitro, amino, amido, $SO_3$, H, SH, SR', wherein R' is independently selected from the same group as $R_1$; carboxy, $C_{1-6}$esters, $C_{1-6}$aldehyde, cyano, $C_{1-6}$alkylamino, $C_{1-6}$dialkylamino, thiol, chloro, bromo, fluoro, iodo, $C_{5-7}$cycloalkyl, $C_{5-7}$cycloalkenyl, $C_{5-7}$cycloalkynyl, $C_{5-11}$aryl, $C_{5-11}$aryl$C_{1-6}$alkyl, and $C_{5-20}$heterocyclyl;

and pharmaceutically acceptable salts thereof.

2. The compound according to claim 1 wherein each of X and Z is independently selected from H, OH, F, Cl and $NH_2$ and Y is selected from OH, F, Cl, $NH_2$ and $C_{2-8}$ alkynyl.

3. The compound according to claim 2 wherein X is $NH_2$, Y is Cl and Z is H.

4. The compound according to claim 2 wherein X is Cl, Y is $NH_2$ and Z is H.

5. The compound according to claim 2 wherein X is $NH_2$, Y is F and Z is H.

6. The compound according to claim 1 wherein one or both of T and T' is F.

7. The compound according to claim 2 wherein X is $NH_2$, Y is $C_{2-8}$alkynyl, Z is H, T is H and T' is OH.

8. The compound according to claim 1 wherein T and T' are each H.

9. The compound according to claim 1 wherein Q is O.

10. The compound according to claim 1 wherein $R_4$ is H.

11. The compound according to claim 1 wherein $R_1$ and $R_2$ are selected such that the moiety $-N-CR_1R_2-COO-$ corresponds to that of a natural amino acid.

12. The compound according to claim 1 wherein each of $R_1$ and $R_2$ is independently selected from Me and H.

13. The compound according to claim 12 wherein one of $R_1$ and $R_2$ is Me and one of $R_1$ and $R_2$ is H such that the C atom bearing $R_1$ and $R_2$ has chirality L as in natural alanine.

14. The compound according to claim 1 wherein Ar is unsubstituted.

15. The compound according to claim 1 wherein Ar is substituted with one, two, three, four, five or more substituents.

16. The compound according to claim 1 wherein Ar is selected from the group consisting of phenyl, pyridyl, naphthyl and quinolyl, each of which may be substituted or unsubstituted.

17. The compound according to claim 1 comprising the diastereoisomer $R_p$, the diastereoisomer $S_p$ or a mixture of the diastereoisomers $R_p$ and $S_p$.

18. A compound selected from the group consisting of:

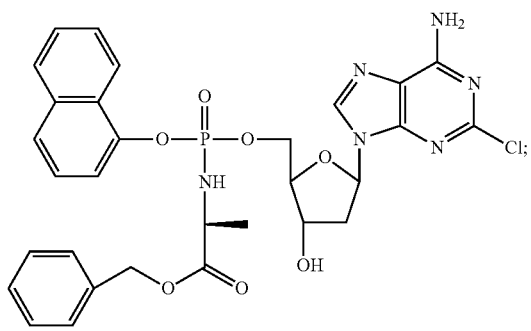

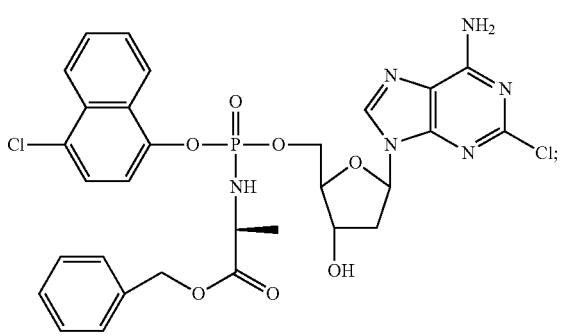

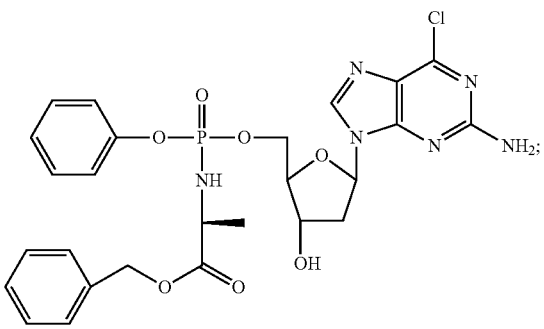

and

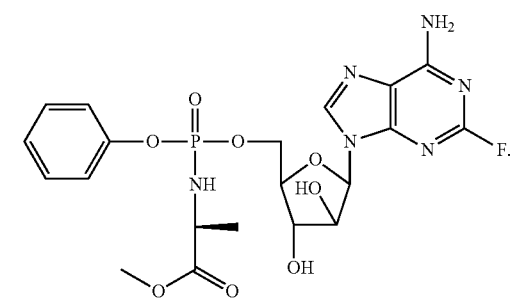

19. The compound:

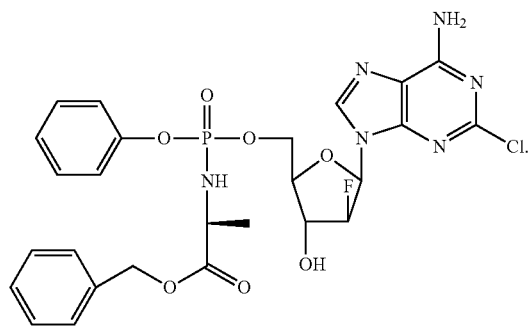

20. A pharmaceutical composition comprising the compound according to claim 1 in combination with a pharmaceutically acceptable carrier, diluent or excipient.

21. A method of treatment of leukaemia, comprising administering to a patient in need of such treatment an effective dose of a compound according to claim 1.

22. A method of treatment of leukaemia comprising administering to a patient in need of such treatment an effective dose of a compound of formula I:

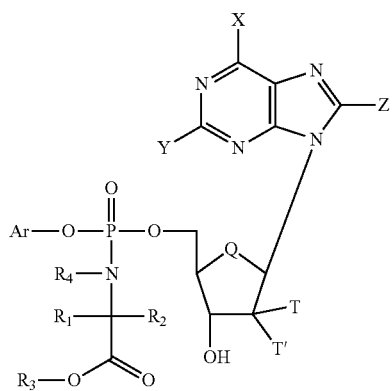

wherein:
each of X and Z is independently selected from H, OH, F, Cl, Br, I, $C_{1-6}$alkyl and $NR_5R_6$, where each of $R_5$ and $R_6$ is independently selected from H and $C_{1-6}$alkyl;
Y is selected from H, OH, F, Cl, Br, I, $C_{1-6}$alkyl, $C_{2-8}$alkynyl, and $NR_5R_6$, where each of $R_5$ and $R_6$ is independently selected from H and $C_{1-6}$ alkyl;
each of T and T' is independently selected from H, F and OH, with the proviso that only one of T and T' can be OH;
Q is selected from O, S and $CR_7R_8$, where $R_7$ and $R_8$ are independently selected from H and $C_{1-6}$ alkyl,
Ar is selected from $C_{6-30}$aryl and $C_{6-30}$heteroaryl, each of which is optionally substituted with one or more substituents independently selected from the group consisting of hydroxy, acyl, acyloxy, nitro, amino, $SO_3H$, SH, SR', wherein R' is independently selected from the same group as $R_1$; carboxyl, $C_{1-6}$ esters, $C_{1-6}$aldehyde, cyano, $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$aryl$C_{1-6}$alkyl, $C_{1-6}$alkyl$C_{5-11}$aryl, $C_{5-11}$aryl, $C_{1-6}$ fluoroalkyl and $C_{2-6}$fluoroalkenyl;
each of $R_1$ and $R_2$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;
each of $R_3$ and $R_4$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;
the optional substituents on $R_1$, $R_2$, $R_3$, and $R_4$ being one or more substituents independently selected from the group consisting of hydroxy, acyl, acyloxy, nitro, amino, amido, $SO_3$, H, SH, SR', wherein R' is independently selected from the same group as $R_1$; carboxy, $C_{1-6}$esters, $C_{1-6}$aldehyde, cyano, $C_{1-6}$alkylamino, $C_{1-6}$dialkylamino, thiol, chloro, bromo, fluoro, iodo $C_{5-7}$cycloalkyl, $C_{5-7}$cycloalkenyl, $C_{5-7}$cycloalkynyl, $C_{5-11}$aryl, $C_{5-11}$aryl$C_{1-6}$alkyl, and $C_{5-20}$heterocyclyl;
and pharmaceutically acceptable salts thereof.

23. A method of preparing a pharmaceutical composition comprising the step of combining an effective dose of a compound according to claim 1 with a pharmaceutically acceptable excipient, carrier or diluent.

24. A process for the preparation of a compound of formula I,

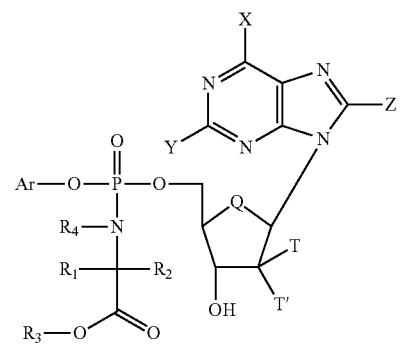

the process comprising the process comprising reacting a compound of formula III:

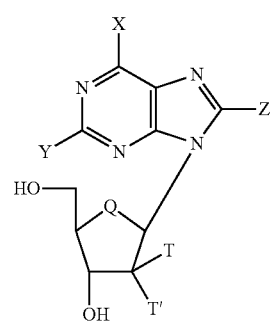

with a compound of formula IV:

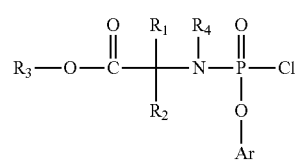

wherein
each of X and Z is independently selected from H, OH, F, Cl, Br, I, $C_{1-6}$alkyl and $NR_5R_6$, where each of $R_5$ and $R_6$ is independently selected from H and $C_{1-6}$alkyl;

Y is selected from OH, F, Cl, Br, I, $C_{1-6}$alkyl, $C_{2-8}$alkynyl, and $NR_5R_6$, where each of $R_5$ and $R_6$ is independently selected from H and $C_{1-6}$ alkyl;

each of T and T' is independently selected from H, F and OH, with the proviso that only one of T and T' can be OH;

Q is selected from O, S and $CR_7R_8$, where $R_7$ and $R_8$ are independently selected from H and $C_{1-6}$alkyl, Ar is selected from $C_{6-30}$aryl and $C_{6-30}$heteroaryl, each of which is optionally substituted with one or more substituents independently selected from the group consisting of hydroxy, acyl, acyloxy, nitro, amino, $SO_3H$, SH, SR', wherein R' is independently selected from the same group as $R_1$; carboxyl, $C_{1-6}$esters, $C_{1-6}$aldehyde, cyano, $C_{1-6}$alkylamino, $C_{1-6}$dialkylamino, thiol, chloro, bromo, fluoro, iodo, $C_{1-6}$alkyl, $C_{2-6}$alkenyl, $C_{1-6}$alkoxy-$C_{1-6}$alkyl, $C_{1-6}$alkoxy-$C_{5-10}$aryl, $C_{5-7}$cycloalkyl, $C_{5-11}$cycloalkyl-$C_{1-6}$alkyl, $C_{5-7}$cycloalkenyl, $C_{5-7}$cycloalkynyl, $C_{5-11}$aryl$C_{1-6}$alkyl, $C_{1-6}$alkyl$C_{5-11}$aryl, $C_{5-11}$aryl, $C_{1-6}$fluoroalkyl and $C_{2-6}$fluoroalkenyl;

each of $R_1$ and $R_2$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;

each of $R_3$ and $R_4$ is independently selected from H, and the group consisting of $C_{1-20}$alkyl, $C_{2-20}$alkenyl, $C_{1-20}$alkoxy, $C_{1-20}$alkoxy$C_{1-20}$alkyl, $C_{1-20}$alkoxy$C_{6-30}$aryl, $C_{2-20}$alkynyl, $C_{3-20}$cycloalkyl$C_{6-30}$aryl, $C_{6-30}$aryloxy and $C_{5-20}$heterocyclyl, any of which is optionally substituted with optional substituents;

the optional substituents on $R_1$, $R_2$, $R_3$, and $R_4$ being one or more substituents independently selected from the group consisting of hydroxy, acyl, acyloxy, nitro, amino, amido, $SO_3$, H, SH, SR', wherein R' is independently selected from the same group as $R_1$; carboxy, $C_{1-6}$esters, $C_{1-6}$aldehyde, cyano, $C_{1-6}$alkylamino, $C_{1-6}$dialkylamino, thiol, chloro, bromo, fluoro, iodo, $C_{5-7}$cycloalkyl, $C_{5-7}$cycloalkenyl, $C_{5-7}$cycloalkynyl, $C_{5-11}$aryl, $C_{5-11}$aryl$C_{1-6}$alkyl, and $C_{5-20}$heterocyclyl.

* * * * *